United States Patent [19]

Lueders

[11] Patent Number: 4,990,605

[45] Date of Patent: * Feb. 5, 1991

[54] METHOD OF MANUFACTURING ALKYLOLIGOGLYCOSIDES

[75] Inventor: Harald Lueders, Recklinghausen, Fed. Rep. of Germany

[73] Assignee: Huels Aktiengesellschaft, Marl, Fed. Rep. of Germany

[*] Notice: The portion of the term of this patent subsequent to Feb. 6, 2007 has been disclaimed.

[21] Appl. No.: 192,600

[22] Filed: May 11, 1988

[30] Foreign Application Priority Data

Sep. 5, 1987 [DE] Fed. Rep. of Germany ....... 3729842

[51] Int. Cl.$^5$ .......................... C07H 1/00; C07H 3/00; C07H 15/00; C07G 3/00
[52] U.S. Cl. .................................. 536/18.5; 536/18.6; 536/124; 536/120
[58] Field of Search ..................... 536/18.5, 18.6, 120, 536/124

[56] References Cited

U.S. PATENT DOCUMENTS

| | | | |
|---|---|---|---|
| 4,349,669 | 9/1982 | Klahr et al. | 536/124 |
| 4,557,729 | 12/1985 | McDaniel Jr., et al. | 536/124 |
| 4,898,934 | 2/1990 | Lueders et al. | 536/18.6 |

FOREIGN PATENT DOCUMENTS 2099390 5/1987 United Kingdom ............... 536/18.6

Primary Examiner—Ronald W. Griffin
Assistant Examiner—Everett White
Attorney, Agent, or Firm—Oblon, Spivak, McClelland, Maier & Neustadt

[57] ABSTRACT

A method of manufacturing alkyloligoglycosides. Alkyloligoglycosides and alkylglycosides having alkyl groups with 8 to 24 carbon atoms, which products are of interest as surface active agents in home economics, and in the cosmetics industry, can be manufactured by glycosidation and transglycosidation. Light-colored alkyloligoglycosides and alkylglycosides can be manufactured by treating their solution in alcohols with activated carbon, distilling off the solvent, and bleaching the distillation residue or an aqueous solution of the residue with a peroxide compound.

12 Claims, No Drawings

METHOD OF MANUFACTURING ALKYLOLIGOGLYCOSIDES

BACKGROUND OF THE INVENTION

1. Field of the Invention

The invention relates to a method which, with the aid of adsorption agents, enables the production of light-colored alkyloligoglycosides and alkylglycosides having alkyl groups with 8 to 24 carbon atoms.

2. Discussion of the Background

Alkyloligoglycosides and alkylglycosides with alkyl groups having 8 to 24 carbon atoms can be prepared partially or completely from many types of raw materials. These alkyloligoglycosides and alkylglycosides are becoming increasingly important, due to their interesting surface active properties combined with very good biodegradability. For use in the home economics and cosmetics sectors, these products must meet stringent esthetic requirements. Therefore methods are sought by which alkyloligoglycosides and alkylglycosides can be produced in aqueous solutions which are transparent and have an attractive color.

For producing alkyloligoglycosides and alkylglycosides with long-chain alkyl groups, one generally first produces alkyloligoglycosides and alkylglycosides with alkyl groups having 1 to 6 carbon atoms. These intermediate products are then converted to the desired alkyloligoglycosides and alkylglycosides by acid-catalyzed transglycosidation, at elevated temperature. However, the products thus produced are dark in color.

According to European Patent No. 165,721, the color of such products can be improved by multistage bleaching with hydrogen peroxide, and can be stabilized by the addition of compounds which liberate sulfur dioxide.

According to European Patent No. 77,167, reducing agents such as hypophosphorous acid or sulfurous acid can be added in the reaction of alcohols with aldoses or ketoses. The color of the alkylglycosides is thereby improved.

Preventive measures are also known. Thus, according to European Patent No. 102,558, one obtains $C_3$ to $C_5$ alkyl glucosides of improved color if the glucosidation is carried out in the presence of an alkali salt of a boron acid.

In preparing long-chain alkylsaccharides, according to U.S. Pat. No. 4,465,828, color improvement can be obtained with the aid of hydroxypolycarboxylic acids such as citric acid, tartaric acid, and malic acid.

According to U.S. Pat. No. 4,483,979, coloring factors can be extracted from alkylpolysaccharides. This costly procedure requires anhydrous polar solvents. In addition, part of the alkylpolysaccharides are extracted in the process, along with the colorants.

The known methods of producing alkyloligoglycosides of improved color are cumbersome, require expensive reagents or else do not lead to the desired color qualities.

SUMMARY OF THE INVENTION

Accordingly, one object of the invention is to provide a simplified and more efficacious method of producing light-colored alkyloligoglycosides and alkylglycosides having alkyl groups with 8 to 24 carbon atoms.

This and other objects of the invention which will become apparent from the following specification have been achieved by the present method of manufacturing light-colored alkyloligoglycosides and alkylglycosides, comprising the steps of:

(i) preparing a neutral or alkaline starting compound mixture, comprising alkylglycosides, alkyloligoglycosides or mixtures thereof and an alcohol solvent;

(ii) contacting this mixture with activated carbon at a temperature from 10°–40° C.;

(iii) separating the activated carbon from the contacted mixture;

(iv) removing the alcohol solvent from the alkylglycosides, alkyloligoglycosides or mixtures thereof; and (v) bleaching the alkylglycosides, alkyloligoglycosides or mixtures thereof with a peroxide compound.

DETAILED DESCRIPTION OF THE PREFERRED EMBODIMENTS

Light-colored alkyloligoglycosides and alkylglycosides can be produced by the present process in which:

(1) The starting compounds for a transglycosidation reaction, in alcoholic solutions, or the products of the transglycosidation, in neutral or alkaline solutions, are treated with activated carbon;

(2) The solvent is distilled off from the treated products; and (3) The residue, or an aqueous preparate of the residue, is bleached with peroxide compounds.

The starting compounds for the transglycosidation are alkylglycosides and alkyloligoglycosides, with mean oligomerization numbers of 1 to approximately 4, having alkyl groups with 1 to 6 carbon atoms. The starting compounds can be derived from hexoses and pentoses such as glucose, mannose, galactose, sorbose, fructose, xylose, ribose, lyxose, lactose, maltose, and arabinose. Preferably the starting compounds are butylglucosides and butyloligoglucosides.

The transglycosidation is generally carried out at 80°–140° C., preferably at 90°–120° C. It may be carried out discontinuously or continuously and is terminated after a (mean) reaction time of 0.5–4 hr.

The products of the transglycosidation, i.e., the alkyloligoglycosides and alkylglycosides having alkyl groups with 8 to 24 carbon atoms, may contain unbranched or branched alkyl groups. They can be produced by transglycosidation with linear or branched primary alcohols having 8 to 24 carbon atoms, and mixtures of the same. Preferably the alcohols contain 8 to 20 carbon atoms.

For example, surface active alcohols originating from natural products, in particular alcohols which are produced by the hydrogenation of fatty acids or fatty acid derivatives, may be used, or entirely synthetic Ziegler alcohols, oxo alcohols, or mixtures of these.

The alkyloligoglycosides and alkylglycosides have mean oligomerization numbers of 1 to 10, and can be derived from the same hexoses and pentoses as the starting compounds for the transglycosidation preferably, the alkyloligoglycosides and alkylglycosides produced have 8 to 24 carbon atoms in the alkyl groups.

In connection with the invention, products having an iodine color number of <30 when in 50% aqueous solution are designated "light-colored".

The solvents used for the starting compounds in the transglycosidation reaction are one or more unbranched or branched primary alcohols with 8 to 24 carbon atoms. For example, surface active alcohols derived from natural products, or entirely synthetic Ziegler alcohols or oxo alcohols may be used.

The glycosidation and transglycosidation reactions are generally conducted using acidic catalysts. Preferred catalysts are strong mineral acids, organic acids and strongly acidic ion exchangers. For example, sulfuric acid or p-toluenesulfonic acid may be used.

The solutions of alkyloligoglycosides and alkylglycosides having alkyl groups with 1 to 6 carbon atoms, preferably in solutions of one or more $C_1$ to $C_6$ alcohols, which are produced in the glycosidation reaction, may be subjected directly to the treatment with activated carbon.

Similarly, the solutions of alkyloligoglycosides and alkylglycosides having alkyl groups with 8 to 24 carbon atoms, in $C_8$ to $C_{24}$ alcohols, which are produced in the transglycosidation reaction, may be used. In this case the solutions must be brought to neutral or alkaline pH by treating with alkali prior to the treatment with activated carbon.

The alcoholic solutions used for the activated carbon treatment have concentrations of 10-90%, preferably 15-40% of the alkyloligoglycosides and alkylglycosides. The treatment is carried out at 10°-140° C., preferably 80°-130° C. In the treatment, activated carbon in the amount of 0.01-10%, based on the weight of the solution, is mixed with the solution. The mixing can be accomplished by stirring or shaking. At the end of the treatment, the activated carbon is removed by known methods, e.g. filtering or centrifuging.

In the case of a continuous process, the solution can be pumped through a bed of activated carbon which is held in place by a suitable filler, sieve, or the like. Up to about 10,000 kg solution can be treated by 1 kg activated carbon. The activated carbon used may be of a commercially available type, e.g. a pulverized or granulated form.

To separate out the solvent, a gentle vacuum distillation is preferably used (100°-150° C., 0.1-10 mbar). This distillation may be carried out, for example, in a rotary or thin layer evaporator.

The residue may be treated with water to form a pumpable solution. The residue or an aqueous preparation of it is bleached with peroxide compounds or solutions thereof, e.g. hydrogen peroxide, peracetic acid, perbenzoic acid, or peroxy disulfuric acid, at 50°-100° C., preferably 70°-90° C. The preferred bleaching agent is hydrogen peroxide.

The present method enables production of light-colored alkyloligoglycosides and alkylglycosides having alkyl groups with 8 to 24 carbon atoms, with low expenditures for apparatus and chemicals, using a process including an adsorption and a bleaching. The products from the method are of high purity and good color quality, and can be used for a wide range of applications. When activated carbon and hydrogen peroxide are used, products are obtained which do not carry additional chemicals, because the activated carbon (which is insoluble) is removed, and the hydrogen peroxide reacts to form water.

Other features of the invention will become apparent in the course of the following descriptions of the exemplary embodiments which are given for illustration of the invention and are not intended to be limiting thereof.

EXAMPLES

Example 1

Preparation of an alkyloligoglycoside solution

In a 500 ml stirred flask fitted with a reflux condenser and a Dean-Stark trap for removing water, 40 g glucose syrup (70% glucose in water), 50 g butylglucoside, 82 g n-butanol, and 1.1 ml 2N sulfuric acid were heated to 110° C. with boiling under reflux. During the process, water was separated out. After 1.5 hr the Fehling's test for glucose was negative.

The reaction mixture, now comprised of a butyloligoglucoside solution in n-butanol, was mixed with 250 g Alfol$^{(R)}$ 1012 (a mixture of about 85% n-decanol, 8.5% n-dodecanol, and 6.5% n-tetradecanol, supplied by the firm Condea, of D-2212 Brunsbuettel) and 8.9 ml 2N butanolic sulfuric acid, and was heated to 110° C. in aspirator vacuum. In the process, n-butanol was distilled off through a short distillation column followed by a descending condenser. After 2.5 hr the transglucosidation was terminated. The reaction mixture was now comprised of an alkyloligoglycoside solution having alkyl groups with 10 to 14 carbon atoms.

Purification of the alkyloligoglycoside solution

The solution was neutralized with 2N sodium hydroxide at 80° C. Then 2 g activated carbon (Article No. 31,616 of the firm Riedel de Haen, D-3016 Seeze) was added, and the mixture was stirred 1 hr at 100° C. and then filtered to remove the activated carbon. The alcohol was then distilled off at 150° C. and 1-2 mbar. A 50% aqueous solution of the alkyloligoglycoside was prepared from the residue by adding an equal weight of water.

100 g of this solution was bleached with 6.7 ml 30% hydrogen peroxide solution, at 80° C. for 1 hr. Thereafter the iodine color number of the solution was 15. After distillation to remove the water, the product obtained was a light-colored material.

Comparison Example A

The procedure was as in Example 1, except that no activated carbon treatment was carried out. The iodine color number of the solution was 80.

Comparison Example B

The procedure was as in Example 1, except that first the alcohol was distilled off and then the activated carbon treatment was carried out on a 50% aqueous alkyloligoglycoside solution (with 2 g activated carbon at 100° C. for 1 hr).

After the bleaching with hydrogen peroxide, the solution had an iodine color number of 40.

Example 2

The procedure was as in Example 1, except that the activated carbon treatment was carried out directly on the butyloligoglucoside solution in n-butanol. The solution had an iodine color number of 20.

Comparison Example C

The procedure was as in Example 1, except that the activated carbon treatment was carried out on the mixture comprised of: butyloligoglucoside solution in n-butanol, Alfol$^{(R)}$ 1012, and 2N butanolic sulfuric acid. The solution had an iodine color number of 60.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United State is:

1. A method of manufacturing light-colored alkyloligoglycosides and alkylglycosides, comprising the steps of:
   (i) preparing a neutral or alkaline starting compound mixture, comprising alkylglycosides, alkyloligoglycosides or mixtures thereof and an alcohol solvent;
   (ii) contacting said mixture with activated carbon at a temperature from 10°–140° C.;
   (iii) separating said activated carbon from said contacted mixture;
   (iv) removing said alcohol solvent from said alkylglycosides, alkyloligoglycosides or mixtures thereof; and
   (v) bleaching said alkylglycosides, alkyloligoglycosides or mixtures thereof with a peroxide compound.

2. The method of claim 1, wherein said alkylglycosides and alkyloligoglycosides comprise $C_{1-6}$ alkylglycosides and $C_{1-6}$ alkyloligoglycosides, and said alcohol solvent comprises at least one or more $C_{1-6}$ alcohols.

3. The method of claim 2, wherein said alkylglycosides and alkyloligoglycosides are butylglucosides and butyloligoglycosides, and said alcohol solvent is n-butanol.

4. The method of claim 1, wherein said alkylglycosides and alkyloligoglycosides comprise $C_{8-24}$ alkylglycosides and $C_{8-24}$ alkyloligoglycosides, and said alcohol solvent comprises one at least $C_{8-24}$ alcohols.

5. The method of claim 4, wherein said alkyl glycosides and said alkyloligoglycosides are alkylglucosides and alkyloligoglucosides.

6. The method of claim 1, wherein said starting compound mixture comprises 10–90 wt. % of said alkylglycosides, alkyloligoglycosides or mixtures thereof.

7. The method of claim 6, wherein said starting compound mixture comprises 15–40 wt. % of said alkylglycosides, alkyloligoglycosides or mixtures thereof.

8. The method of claim 1, wherein 0.01–10 wt. % activated carbon based on the weight of said mixture is used in said contacting step.

9. The method of claim 1, wherein said contacting step is carried out at temperature of 80°–130° C.

10. The method of claim 1, wherein said bleaching step is conducted with hydrogen peroxide at 50°–100° C.

11. The method of claim 1, wherein said starting compound mixture comprises $C_{1-6}$ alkylglycosides, alkyloligoglycosides or mixtures thereof, said alcohol solvent is a $C_{8-24}$ alcohol, and said starting compound mixture is subjected to transglycosidation to prepare $C_{8-24}$ alkylglycosides, alkyloligoglycosides, or mixtures thereof before said contacting step.

12. The method of claim 11, wherein said transglycosidation is carried out at 80°–140° C. for 0.5–4 hours.

* * * * *

UNITED STATES PATENT AND TRADEMARK OFFICE
CERTIFICATE OF CORRECTION

PATENT NO. : 4,990,605

DATED : FEBRUARY 5, 1991

INVENTOR(S) : Harald LUEDERS

It is certified that error appears in the above-identified patent and that said Letters Patent is hereby corrected as shown below:

```
Column 6, line 6, "one at least" should read
                --at least one--.
```

Signed and Sealed this

First Day of December, 1992

Attest:

DOUGLAS B. COMER

*Attesting Officer*  *Acting Commissioner of Patents and Trademarks*